United States Patent

Kawamura et al.

Patent Number: 5,360,912
Date of Patent: Nov. 1, 1994

[54] PROCESS OF PRODUCING IMINOTHIAZOLINE DERIVATIVES

[75] Inventors: Shinichi Kawamura, Osaka; Junichi Sato, Toyonaka; Yuzuru Sanemitsu, Ashiya, all of Japan

[73] Assignee: Sumitomo Chemical Company, Limited, Osaka, Japan

[21] Appl. No.: 17,259

[22] Filed: Feb. 12, 1993

[51] Int. Cl.$^5$ .......................... C07D 277/40
[52] U.S. Cl. .................................. 548/199
[58] Field of Search ........................ 548/199

[56] References Cited

U.S. PATENT DOCUMENTS 3,167,564  1/1965  Yura ........................ 548/199

FOREIGN PATENT DOCUMENTS 0446802  9/1991  European Pat. Off. .

OTHER PUBLICATIONS

Chemical Abstracts, vol. 82, 1975, 140117m.

Primary Examiner—Robert Gerstl

[57] ABSTRACT

There is disclosed a process for producing an iminothiazoline derivative of the general formula:

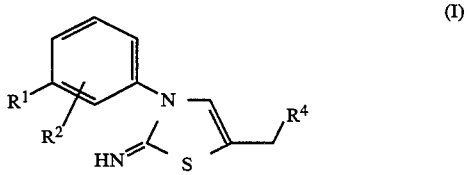

(I)

wherein $R^1$ is halogen, halo(lower)alkyl, halo(lower)alkoxy or halo(lower)alkylthio; $R^2$ is hydrogen or halogen; and $R^4$ is hydrogen or lower alkyl. This compound (I) can be obtained by cyclization of a thiourea derivative of the general formula:

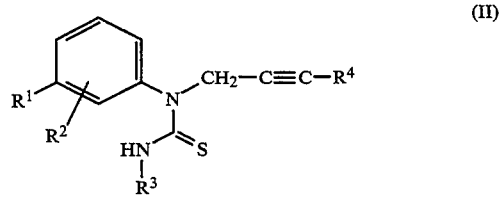

(II)

wherein $R^1$, $R^2$ and $R^4$ are each the same as defined above, and $R^3$ is hydrogen or (lower)alkylcarbonyl optionally substituted with at least one substituent selected from the group consisting of halogen, lower alkyl and lower alkoxy.

7 Claims, No Drawings

PROCESS OF PRODUCING IMINOTHIAZOLINE DERIVATIVES

FIELD OF THE INVENTION

The present invention relates to a process of producing iminothiazoline derivatives which are useful as intermediates for production of herbicidal compounds.

BACKGROUND OF THE INVENTION

It is well known that an iminothiazoline derivative of the general formula:

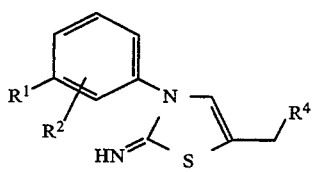
(I)

wherein $R^1$ is halogen or halo(lower)alkyl, halo(lower)alkoxy or halo(lower)alkylthio; $R^2$ is hydrogen or halogen; and $R^4$ is hydrogen or lower alkyl, is useful as an intermediate for production of herbicidal compounds (see, e.g., European Patent Publication No. 446802).

SUMMARY OF THE INVENTION

The present inventors have intensively studied and found that such an iminothiazoline derivative can be obtained with high yield in a simple and easy way by cyclization of a particular thiourea derivative, thereby completing the present invention.

That is, the present invention provides a process for producing an iminothiazoline derivative of the general formula:

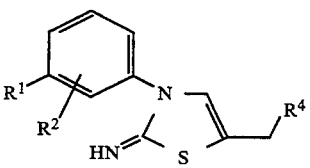
(I)

wherein $R^1$, $R^2$ and $R^4$ are each the same as defined above, the process comprising the steps of subjecting a thiourea derivative of the general formula:

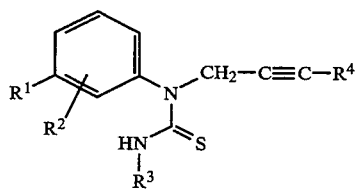
(II)

wherein $R^1$, $R^2$ and $R^4$ are each the same as defined above, and $R^3$ is hydrogen or (lower)alkylcarbonyl optionally substituted with at least one substituent selected from the group consisting of halogen, lower alkyl and lower alkoxy, to cyclization by acid treatment.

A preferred class of iminothiazoline derivatives to be prepared by the process of the present invention are those wherein $R^1$ is halogen, halo($C_1$-$C_6$)alkyl, halo($C_1$-$C_6$)-alkoxy or halo($C_1$-$C_6$)alkylthio; $R^2$ is hydrogen or halogen; and $R^4$ is hydrogen or $C_1$-$C_6$ alkyl. A preferred class of thiourea derivatives to be used as a starting material are those wherein $R^1$, $R^2$ and $R^4$ are each the same as defined just above, and $R^3$ is hydrogen or $C_1$-$C_6$ alkylcarbonyl optionally substituted with at least one substituent selected from the group consisting of halogen $C_1$-$C_6$ alkyl and $C_1$-$C_6$ alkoxy.

DETAILED DESCRIPTION OF THE INVENTION

The process of the present invention is characterized in that a particular thiourea derivative is subjected to cyclization by acid treatment. According to this process, the reaction is carried out in a short step for a short period of time, and iminothiazoline derivatives can be obtained with high yield in a simple and easy way.

The cyclization is usually carried out in a solvent at a temperature of 0° to 100° C., preferably 40° to 80° C., for a period of 1 to 20 hours. More preferably, the reaction is started at a temperature of 40° to 60° C., and then, the temperature is increased to 60° to 80° C. The thiourea derivative (II) is typically treated with an aqueous solution of an acid at a proportion of 1 to 1000 equivalents of the acid to one equivalent of the thiourea derivative (II).

Examples a of the solvent which can be used are aromatic hydrocarbons such as benzene, toluene and xylene; ethers such as diethyl ether, diisopropyl ether, dioxane, tetrahydrofuran and diethylene glycol dimethyl ether; fatty acids such as formic acid, acetic acid and oleic acid; alcohols such as methanol, ethanol, isopropanol, t-butanol, octanol, cyclohexanol, methoxy ethanol, diethylene glycol and glycerol; water which is preferred, and the like. These solvents may be used solely or in any combination.

Typically, the thiourea derivative (II) is treated with an aqueous solution of an inorganic acid such as hydrochloric acid or sulfuric acid. A preferred example of the acid is sulfuric acid, more particularly sulfuric acid having a concentration of 80% to 99%.

After completion of the reaction, the reaction mixture may be subjected to an ordinary post-treatment such as extraction with an organic solvent and concentration, and if necessary, any purification such as chromatography may be further utilized to give the objective compound (I).

The substituents $R^1$, $R^2$, $R^3$ and $R^4$ are not particularly limited.

Typical examples of the iminothiazoline derivatives produced by the process of the present invention are shown in Table 1.

TABLE 1

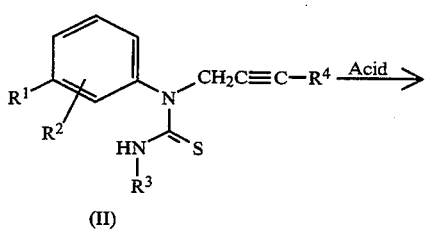
(II)

TABLE 1-continued

![structure I]

| R¹ | R² | R³ | R⁴ |
| --- | --- | --- | --- |
| CF₃ | H | COCH₃ | H |
| CF₃ | H | COCH₃ | CH₃ |
| CF₃ | H | COC₂H₅ | H |
| CF₃ | 4-F | COCH₃ | H |
| CF₃O | H | COCH₃ | CH₃ |
| Cl | 4-F | COCH₃ | CH₃ |

In the process of the present invention, the thiourea derivative (II) as the starting material can be produced as follows: (see, e.g., Japanese Patent Application No.211953/1991)

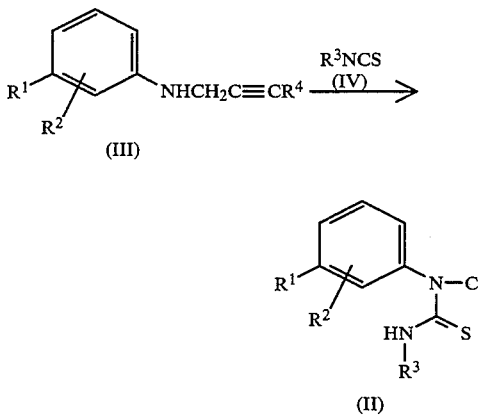

wherein $R^1$, $R^2$, $R^3$ and $R^4$ are each the same as defined as above.

That is, the thiourea derivative (II) can be obtained by reacting the aniline derivative (III) with the isothiocyanate compound (IV).

This reaction is usually carried out in a solvent at a temperature of 0° to 200° C. for a period of 1 to 30 hours. The isothiocyanate compound (IV) is typically used at a proportion of 1 to 1.5 equivalents to one equivalent of the aniline derivative (III).

Examples of the solvent which can be used are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane and diethylene glycol dimethyl ether; ketones such as acetone, methyl ethyl ketone, methyl isobutyl ketone, isophorone and cyclohexanone; nitro compounds such as nitroethane and nitrobenzene; tertiary amines such as N,N-diethylaniline, tributylamine and N-methylmorpholine; acid amides such as N,N-dimethylformaide; and sulfur compounds such as dimethylsulfoxide and sulforan. These solvents may be used solely or in any combination.

After completion of the reaction, the reaction mixture may be subjected to an ordinary post-treatment in the same manner as described above.

The present invention will be further explained by way of the following EXAMPLE and Reference EXAMPLE, which are not to be construed to limit the scope thereof.

EXAMPLE 1

Acetyl chloride (2.75 g) was mixed with acetonitrile (70 ml), and the mixture was cooled to 0° C. Then, potassium thiocyanate (3.75 g) was added thereto, and the mixture was stirred at room temperature for 6 hours. After cooling to 0° C. again, 3-trifluoromethyl-N-propargyl-aniline (7 g) was added thereto, and the mixture was stirred at room temperature for 3 hours. After the solvent was distilled off under reduced pressure, the residue was extracted with ethyl acetate (300 ml), and the extract was washed with water. The solvent was distilled off to give N-[3-(trifluoromethyl)phenyl]-N-propargyl-N'-acetylthiourea as crystallines (8 g). This identification was achieved by proton nuclear magnetic resonance (¹H-NMR).

These crystallines (8 g) were mixed with an 85% aqueous solution (8 ml) of sulfuric acid and the mixture was stirred at 40° C. for 1 hour, then at 60° to 80° C. for 4 hours.

After completion of the reaction, the reaction mixture was poured into ice water. The mixture was neutralized with aqueous sodium hydroxide and extracted with ethyl acetate (50 ml×3). The extract was dried over anhydrous magnesium sulfate and the solvent was distilled off to give 3-[3-(trifluoromethyl)phenyl]-5-methyl-2-iminothiazoline as oil (6 g). ¹H-NMR (CDCl₃, TMS): δ7.7 (4H), 6.5 (1H), 2.2 (s, 3H).

EXAMPLE 2

Acetyl chloride (2.75 g) is mixed with acetonitrile (70 ml), and the mixture is cooled to 0° C. Then, potassium thiocyanate (3.75 g) is added thereto, and the mixture is stirred at room temperature for 6 hours. After cooling to 0° C. again, 3-trifluoromethyl-N-propargylaniline (7 g) is added thereto, and the mixture is stirred at room temperature for 3 hours. After the solvent is distilled off under reduced pressure, the residue is extracted with ethyl acetate (300 ml), and the extract is washed with water. The solvent is distilled off to give N-[3-(trifluoromethyl)phenyl]-N-propargyl-N'-acetylthiourea as crystallines (8 g). This identification is achieved by proton nuclear magnetic resonance (¹H-NMR).

These crystallines (8 g) are mixed with an 95% aqueous solution (8 ml) of sulfuric acid and the mixture is stirred at 40° C. for 1 hour, then at 60° to 80° C. for 4 hours.

After completion of the reaction, the reaction mixture is poured into ice water. The mixture is neutralized with aqueous sodium hydroxide and extracted with ethyl acetate (50 ml×3). The extract is dried over anhydrous magnesium sulfate and the solvent is distilled off to give 3-[3-(trifluoromethyl)phenyl]-5-methyl-2-iminothiazoline as oil.

EXAMPLE 3

Acetyl chloride (2.75 g) is mixed with acetonitrile (70 ml), and the mixture is cooled to 0° C. Then, potassium thiocyanate (3.75 g) is added thereto, and the mixture is stirred at room temperature for 6 hours. After cooling to 0° C. again, 3-trifluoromethyl-N-propargylaniline (7 g) is added thereto, and the mixture is stirred at room temperature for 3 hours. After the solvent is distilled off under reduced pressure, the residue is extracted with ethyl acetate (300 ml), and the extract is washed with water. The solvent is distilled off to give N-[3-(trifluoromethyl)phenyl]-N-propargyl-N'-acetylthiourea as crystallines (8 g). This identification is achieved by proton nuclear magnetic resonance ($^1$H-NMR ).

These crystallines (8 g) are mixed with an 85% aqueous solution (8 ml) of sulfuric acid and the mixture is stirred at 60° C. for 1 hour, then at 60° to 80° C. for 4 hours.

After completion of the reaction, the reaction mixture is poured into ice water. The mixture is neutralized with aqueous sodium hydroxide and extracted with ethyl acetate (50 ml×3). The extract is dried over anhydrous magnesium sulfate and the solvent is distilled off to give 3-[3-(trifluoromethyl)phenyl]-5-methyl-2-iminothiazoline as oil.

REFERENCE EXAMPLE

3-[3-(Trifluoromethyl)phenyl]-5-methyl-2-iminothiazoline (6 g) obtained in Example 1 was dissolved in ethyl acetate (100 ml). Then, trifluoroacetic anhydride (5 g) was added to this solution at room temperature and the mixture was stirred for 1 hour.

After completion of the reaction, the solvent was distilled off under reduced pressure and ice water was poured to the residue. The resulting crystallines were recrystallization from isopropanol to give 3-[3-(trifluoromethyl)phenyl]-2-(trifluoroacetyl)imino-5-methylthiazoline (6 g); m.p., 128° C.

The product thus obtained is useful as a herbicide.

What is claimed is:

1. A process for producing an iminothiazoline derivative of the formula:

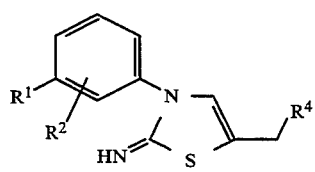

wherein $R^1$ is halogen, halo(lower)alkyl, halo(lower)alkoxy or halo(lower)alkylthio; $R^2$ is hydrogen or halogen; and $R^4$ is hydrogen or lower alkyl, the process comprising the steps of subjecting a thiourea derivative of the general formula:

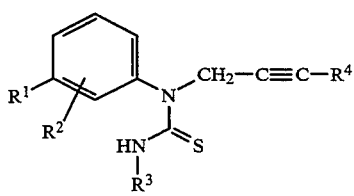

wherein $R^1$, $R^2$ and $R^4$ are each the same as defined above, and $R^3$ is hydrogen or (lower)alkylcarbonyl optionally substituted with at least one substituent selected from the group consisting of halogen, lower alkyl and lower alkoxy, to cyclization by acid treatment.

2. The process for producing an iminothiazoline derivative of the general formula:

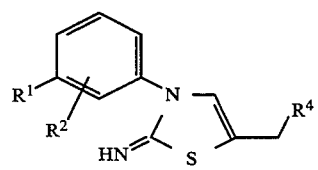

wherein $R^1$ is halogen, halo($C_1$-$C_6$)alkyl, halo($C_1$-$C_6$)alkoxy or halo(C1-C6)alkylthio; $R^2$ is hydrogen or halogen; and $R^4$ is hydrogen or $C_1$-$C_6$ alkyl, the process comprising the steps of subjecting a thiourea derivative of the general formula:

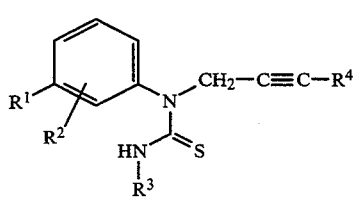

wherein $R^1$ , $R^2$ and $R^4$ are each the same as defined above, and $R^3$ is hydrogen or ($C_1$-$C_6$ alkyl)carbonyl optionally substituted with at least one substituent selected from the group consisting of halogen, $C_1$-$C_6$ alkyl and $C_1$-$C_6$ alkoxy, to cyclization by acid treatment.

3. The process according to claim 1, wherein the thiourea derivative is treated with an aqueous solution of sulfuric acid.

4. The process according to claim 1, wherein the thiourea derivative is treated with an aqueous solution of hydrochloric acid .

5. The process according to claim 3, wherein the thiourea derivative is treated with an aqueous solution of sulfuric acid having a concentration of 80% to 99%.

6. The process according to claim 5, wherein the acid treatment is carried out at a temperature of 40° to 80° C.

7. The process according to claim 1, wherein $R^1$ is trifluoromethyl, $R^2$ is hydrogen, $R^3$ is acetyl and $R^4$ is hydrogen.

* * * * *